United States Patent [19]

Al-Sioufi et al.

[11] Patent Number: 4,998,925
[45] Date of Patent: Mar. 12, 1991

[54] I. V. CONNECTOR

[76] Inventors: Habib Al-Sioufi, P.O. Box 654, Brookline, Mass. 02146; Antoine J. Koudsi, 52 Blueberry Cir., Pelham, N.H. 03076

[21] Appl. No.: 198,293

[22] Filed: May 24, 1988

[51] Int. Cl.⁵ .................................. A61M 25/00
[52] U.S. Cl. .......................... 604/283; 604/192; 604/240; 604/905
[58] Field of Search ............... 604/240, 280, 283, 263, 604/192, 197, 198, 407, 414, 905

[56] References Cited

U.S. PATENT DOCUMENTS

| 3,610,241 | 10/1971 | LeMarie | 604/407 |
| 3,993,063 | 11/1976 | Larrabee | 604/197 |
| 4,316,462 | 2/1982 | Baker | 604/192 |
| 4,675,020 | 6/1987 | McPhee | 604/414 |
| 4,693,708 | 9/1987 | Wanderer et al. | 604/198 |
| 4,762,516 | 9/1988 | Luther et al. | 604/164 |
| 4,776,849 | 10/1988 | Shinro et al. | 604/283 |
| 4,790,827 | 12/1988 | Haber et al. | 604/198 |
| 4,828,548 | 5/1989 | Walter | 604/164 |
| 4,932,944 | 6/1990 | Jagger et al. | 604/192 |

Primary Examiner—C. Fred Rosenbaum
Assistant Examiner—Kathleen A. Daley
Attorney, Agent, or Firm—James J. Brown

[57] ABSTRACT

A connector is described for intravenous systems which fits over an I.V. needle which is inserted into the system such that the I.V. needle is at all times covered to prevent accidental contact with those using the system. The connector is a sleeve which fits over the I.V. needle and completely covers it. One end of the catheter tube or adaptor fitted to the tube is inserted into the sleeve so that the I.V. needle becomes engaged with the tube.

3 Claims, 2 Drawing Sheets

I. V. CONNECTOR

SUMMARY OF THE INVENTION

The present invention is directed to a device for connecting an IV needle into an intravenous line or an adapter for an intravenous line in which the needle is at all times completely covered to avoid inadvertent injury or contact. More specifically, the present invention is directed to an IV connector which is essentially a sleeve which fits completely over an IV needle and permits engagement with an IV line which may be inserted into a vein such that the IV needle connected into the line is at no time exposed.

BACKGROUND OF THE INVENTION

Patients frequently require either continuous or temporary IV access for the delivery of medications, fluid, nutritional material or the withdrawal periodically of blood samples. In these situations, it is usually the practice to insert an IV line into the vein and leave it in place over a period of time so as to avoid the need for making continuous new punctures. Such IV lines are usually equipped with provision for insertion of an IV needle into the line for periodic or continuous delivery of the medication, fluid or withdrawal of blood.

When a needle is used in the manner described as a means for introducing or withdrawing material into an IV system already in place, the health care provider is required to hold the outlet or adapter of the IV system in one hand and insert the exposed needle with the other hand. This procedure, however, exposes the health care provider to the hazard of coming into contact with the sharp exposed needle or even puncturing himself with it. This can be particularly hazardous in situations where blood is being withdrawn through the IV system and the health care provider may therefore become exposed to blood which can be contaminated with viruses, or other contagious diseases or contaminants.

It is accordingly an object of the present invention to provide an improved IV connector system in which the needle used to introduce or withdraw material from an IV line is at no time exposed. It is a further object of the present invention to provide an IV connector which permits the health care provider to connect an IV needle into an IV line easily and quickly without any hazard of coming into contact with the exposed needle or puncturing himself in the process.

DISCUSSION OF THE PRIOR ART

U.S. Pat. No. 4,682,981 to Suzuki et al. provides a medical device which facilitates introducing a catheter into a blood vessel.

U.S. Pat. No. 4,072,146 to Howes is concerned with a catheter device which can deliver several different fluids and which can be connected to a syringe without the use of a needle.

U.S. Pat. No. 4,177,809 to Moorehead is concerned with an intravenous catheter which controls precisely the placement of the catheter tube within the body of a patient to accommodate fluid flow into or out of the person.

U.S. Pat. No. 4,701,160 to Lindsay et al. is concerned with a catheter for infusing blood into a patient which has first and second inlet openings, an outlet opening and a passage way connecting the respective openings along with a valve member between the inlet openings.

DETAILED DESCRIPTION OF THE PRESENT INVENTION

In accordance with the present invention, a connector is provided for facilitating the use of an IV needle in an intravenous catheter system. The IV connector of the present invention essentially comprises an elongated cylindrical sleeve which is open at both ends and which is adapted at one of its ends to enclose an IV needle such that the needle is completely disposed within the sleeve and to receive at its other end a portion of an IV line such that the IV line is held within the sleeve in engagement with the needle. The connector of the present invention completely envelopes the IV needle at all times and protects the medical provider using the device from possible contact or injury.

The invention will, however, be more fully appreciate by having reference in detail to the drawings provided herein which depict a preferred embodiment thereof.

Figure 1:
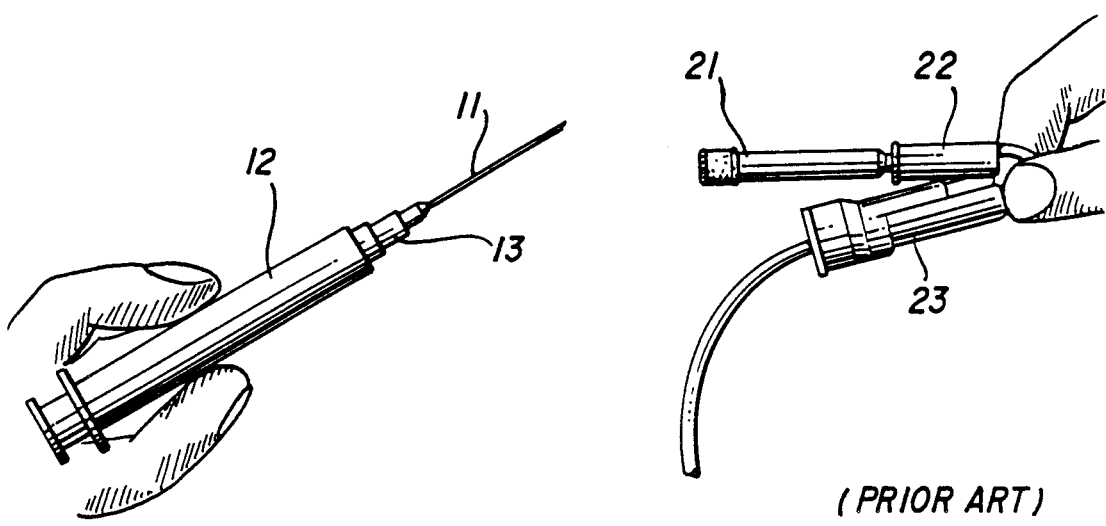
FIG. 1 illustrates an IV catheter system of the prior art prepared for insertion of a needle into the IV line.
Figure 2:
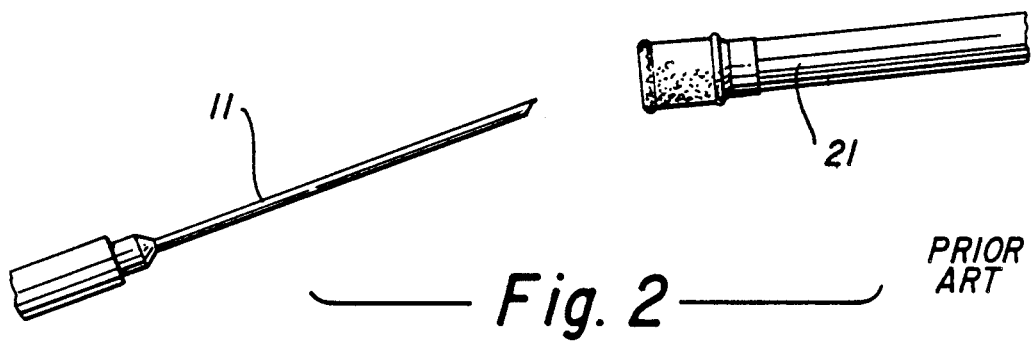
FIG. 2 is a close up view illustrating an exposed syringe needle ready for insertion into an IV connector of the prior art.
Figure 3:
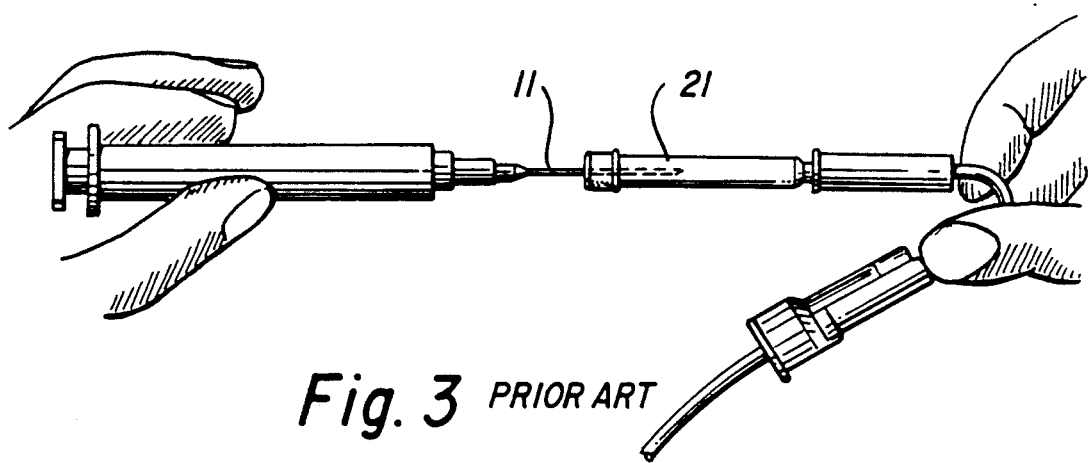
FIG. 3 illustrates an IV catheter system with the needle and syringe inserted into the system.

Directing attention to FIGS. 1, 2 and 3 which illustrate devices of the prior art, FIG. 1 of the drawings shows a standard IV line at 23, having a connector 22 with an adapter inserted therein at 21 for receiving an IV needle 11 which is part of syringe 12. As can be seen more clearly in FIG. 2, the adapter 21 is provided with a rubber cap which can be punctured by the needle 11. In FIG. 3, the exposed needle 11 has been inserted through the rubber cap in the adapter 21 so that the syringe 12 is now connected into the IV line 23. As will further be appreciated by a consideration of FIGS. 1, 2 and 3, placement of the needle 11 into the IV line necessitates exposure of the needle with the conncomminent hazard of contact or injury to the individual performing the operation.

Figure 4:
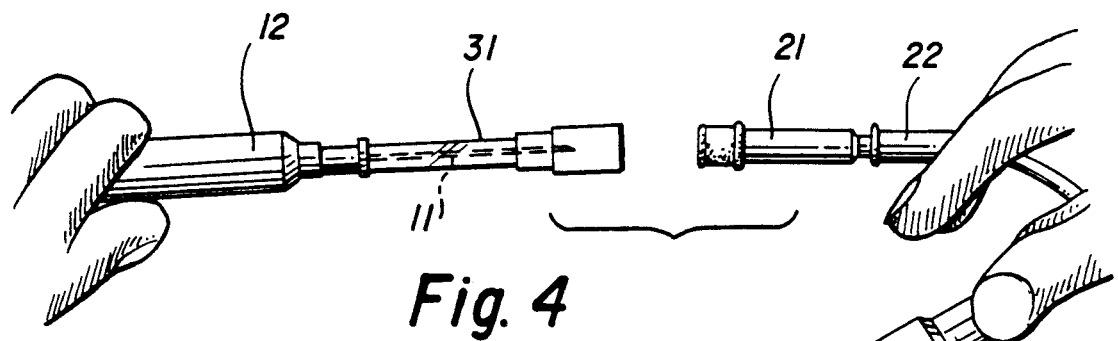
FIG. 4 illustrates the IV connector of the present invention in place covering a needle and ready for connection into an IV line.
Figure 5:
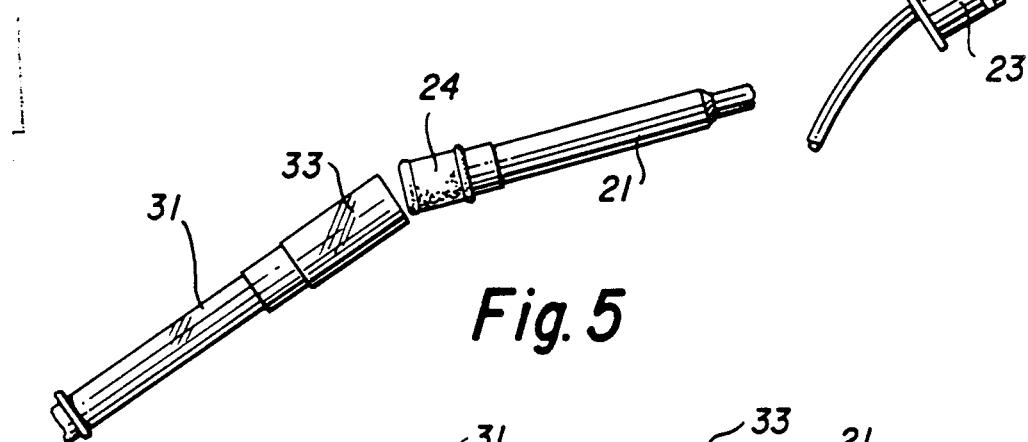
FIG. 5 is a close up view of the connector of the present invention just prior to connection into an IV line.
Figure 6:
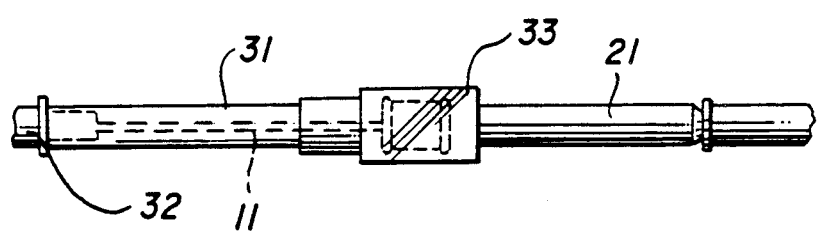
FIG. 6 illustrates the IV connector of the present invention used to connect a needle into an IV line and already in place and ready for use.
Figure 7:
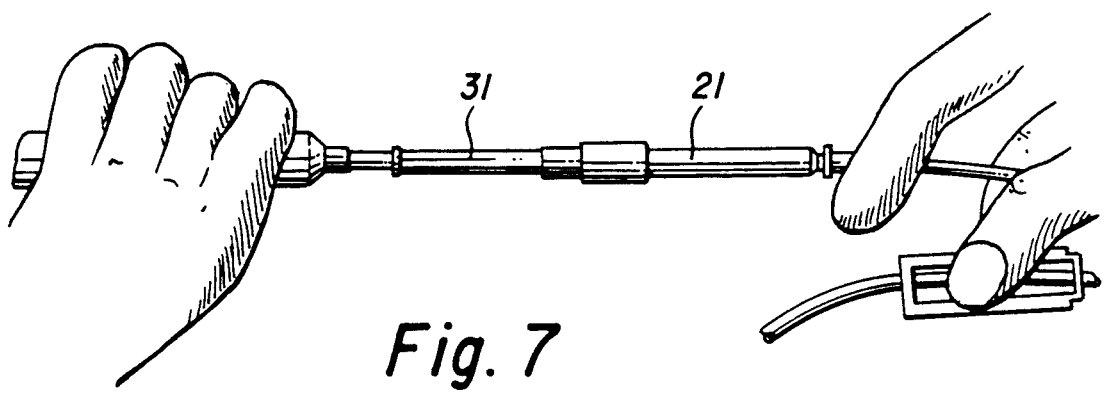
FIG. 7 is an additional view of the connector of FIG. 6.

Directing attention now to FIGS. 4 through 7, it will be seen that needle 11 in FIG. 4 is completely covered by cylindrical sleeve 31 which is open at both of its ends so that the end 32 fits snugly around the neck of the syringe 12 or the collar of needle 11 while the other end 33 of the sleeve has an internal diameter just sufficient to receive adapter 21. Thus, at no time is needle 11 actually exposed so that it can come into contact with the individual using the system. In actual operation, the rubber cap end 24 of adapter 21 is simply inserted into the end 33 of connector 31 so that the needle 11 actually pierces the cap 24 to make proper engagement with the IV system. The overall system of the present invention in which syringe 12 is connected into IV line 23 is illustrated in its entirety in FIG. 7 of the drawings.

It will, of course, be appreciated that sleeve 31 can be provided in different sizes, shapes and designs to fit different adapters and outlet systems of IV systems which are in use. The present invention, however, contemplates that in all such connectors, the exposed needle is completely covered at all times by a sleeve irrespective of the configuration, size and shape of the sleeve so that there is no hazard of contact to the health care provider using the device. In all instances, the IV system being used is inserted into the open end of the sleeve a sufficient distance to engage the sleeve and the needle residing therein.

While a preferred embodiment of the present invention has been illustrated and described herein, it will be apparent to those of ordinary skill in the art that various modifications can be made within the scope of the present invention as defined in the claims appended hereto.

We claim:

1. An I.V. system for withdrawing from or injecting into a body material which system comprises in combination: an elongated catheter tube with means at one end for insertion into said body, and one or more means disposed along said tube or at the other terminus thereof for connecting said tube with a reservoir for said material, said connecting means including an I.V. needle disposed within and completely covered by an elongated sleeve with an open end for receiving said catheter and engaging it with said needle within said connector means such that a fluid passage is provided between said reservoir and said catheter tube.

2. The system of claim 1 wherein said reservoir and I.V. needle are a syringe.

3. The system of claim 1 wherein said insertion means is a hollow needle.

* * * * *